(12) United States Patent
Bauer et al.

(10) Patent No.: US 7,420,007 B2
(45) Date of Patent: *Sep. 2, 2008

(54) DIALKYLPHOSPHINIC SALTS

(75) Inventors: Harald Bauer, Kerpen (DE); Werner Krause, Huerth (DE); Martin Sicken, Cologne (DE); Norbert Weferling, Huerth (DE)

(73) Assignee: Clariant Produkte (Deutschland) GmbH, Sulzbach (DE)

( * ) Notice: Subject to any disclaimer, the term of this patent is extended or adjusted under 35 U.S.C. 154(b) by 458 days.

This patent is subject to a terminal disclaimer.

(21) Appl. No.: 11/015,195

(22) Filed: Dec. 17, 2004

(65) Prior Publication Data
US 2006/0074157 A1    Apr. 6, 2006

(30) Foreign Application Priority Data
Dec. 19, 2003   (DE) ............................. 103 59 814

(51) Int. Cl.
*C08K 5/5313* (2006.01)
(52) U.S. Cl. .................. 524/126; 524/133; 252/609
(58) Field of Classification Search ............... 524/126, 524/133; 252/609
See application file for complete search history.

(56) References Cited

U.S. PATENT DOCUMENTS

| | | | |
|---|---|---|---|
| 2,957,931 A | 10/1960 | Hamilton et al. | |
| 3,914,345 A | 10/1975 | Kleiner et al. | |
| 4,036,811 A | 7/1977 | Noetzel et al. | |
| 4,138,433 A | 2/1979 | Kleiner et al. | |
| 5,780,534 A | 7/1998 | Kleiner et al. | |
| 6,013,707 A | 1/2000 | Kleiner et al. | |
| 6,096,914 A | 8/2000 | Seitz | |
| 6,184,405 B1 | 2/2001 | Kleiner et al. | |
| 6,207,736 B1 | 3/2001 | Nass et al. | |
| 6,255,371 B1 | 7/2001 | Schlosser et al. | |
| 6,270,560 B1 | 8/2001 | Kleiner et al. | |
| 6,300,516 B1 | 10/2001 | Weferling et al. | |
| 6,329,544 B1 | 12/2001 | Weferling et al. | |
| 6,355,832 B1 | 3/2002 | Weferling et al. | |
| 6,359,171 B1 | 3/2002 | Weferling et al. | |
| 6,365,071 B1 | 4/2002 | Jenewein et al. | |
| 6,534,673 B1 | 3/2003 | Weferling et al. | |
| 6,547,992 B1 | 4/2003 | Schlosser et al. | |
| 6,753,363 B1 | 6/2004 | Harashina | |
| 2004/0049063 A1 | 3/2004 | Hoerold et al. | |
| 2005/0009941 A1 | 1/2005 | Sicken et al. | |
| 2005/0137418 A1 * | 6/2005 | Bauer et al. ............... | 562/8 |

FOREIGN PATENT DOCUMENTS

| | | |
|---|---|---|
| DE | 2100779 | 7/1972 |
| DE | 2447727 | 4/1976 |
| DE | 2827867 | 1/1980 |
| DE | 19614424 | 10/1997 |
| DE | 19734437 | 2/1999 |
| DE | 19920276 | 11/2000 |
| DE | 19933901 | 2/2001 |
| DE | 10241373 | 3/2004 |
| EP | 0699708 | 3/1996 |
| EP | 1024167 | 8/2000 |
| EP | 1055676 | 11/2000 |
| EP | 1479718 | 11/2004 |
| WO | WO 96/16948 | 6/1996 |
| WO | WO 98/13371 | 4/1998 |
| WO | WO 98/08898 | 5/1998 |
| WO | WO 98/20012 | 5/1998 |
| WO | WO 98/39381 | 9/1998 |
| WO | WO 98/45364 | 10/1998 |
| WO | WO 99/28327 | 6/1999 |
| WO | WO 99/28328 | 6/1999 |

OTHER PUBLICATIONS

U.S. Appl. No. 11/016,663, by Bauer et al., filed Dec. 17, 2004.
EPO Search Report for EP 04028906, mailed Mar. 16, 2005.
Drinkard, "Some Salts of Symmetric Phosphic Acids", Journal of the American Chemical Society, pp. 5520, 5521 (Nov. 1952).
German Office Action for DE 10359814.6, mailed Aug. 24, 2004.
E.E. Nifante'ev et al., "Journal of General Chemistry USSR" 50(8) pp. 1416-1423(1980).
Co-pending U.S. Appl. No. 11/714,482; by Maas et al. filed Mar. 6, 2007.

(Continued)

*Primary Examiner*—Peter Szekely
(74) *Attorney, Agent, or Firm*—Anthony A. Bisulca

(57) ABSTRACT

The invention relates to dialkylphosphinic salts of the formula (I)

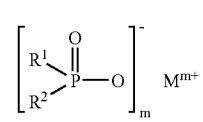

(I)

where
R$^1$, R$^2$ identical or different, are C$_1$-C$_6$-alkyl, linear or branched
M is Mg, Ca, Al, Sb, Sn, Ge, Ti, Fe, Zr, Zn, Ce, Bi, Sr, Mn, Li, Na, K and/or is a protonated nitrogen base;
m is from 1 to 4;
wherein the telomer content is from 0.01 to 6% by weight.

The invention also relates to glare use in flame retardant compositions, and to flame-retardant polymer molding compositions and flame-retardant polymer moldings which comprise these dialkylphosphinic salts.

42 Claims, No Drawings

OTHER PUBLICATIONS

Co-pending U.S. Appl. No. 11/714,481; by Maas et al. filed Mar. 6, 2007.
Co-pending U.S. Appl. No. 11/714,331; by Maas et al. filed Mar. 6, 2007.
EPO Search Report for EP 04028905, mailed Apr. 11, 2005.
Office Action for U.S. Appl. No. 11/016,663 dated Jul. 12, 2007.
U.S. Appl. No. 11/182,459, by Bauer et al., filed Jul. 15, 2005.
US 6,248,921, 06/2001, Weferling et al. (withdrawn)

* cited by examiner

DIALKYLPHOSPHINIC SALTS

The invention relates to dialkylphosphinic salts and their use in flame retardant compositions, and also to flame-retardant polymer molding compositions and to flame-retardant polymer moldings which comprise these dialkylphosphinic salts.

Dialkylphosphinic salts and processes for their preparations are known. For example, WO 99/28327 describes a process which starts from alkali metal salts of hypophosphorous acids and leads to phosphinic salts in two stages. These comprise traces of the solvent (acetic acid) as contaminants in the final product, and these leads to undesired side effects in the intended incorporation into plastics. Furthermore, phosphinic salts of that prior art comprise undesired telomeric by-products arising from the use of organic solvents in the first stage of the process.

It is therefore an object of the present invention to provide dialkylphosphinic salts of certain metals with particularly low content of residual solvent, in particular acetic acid, and of telomeric products.

Surprisingly, it has been found that dialkylphosphinic salts with particularly low content of residual solvent (acetic acid) and of telomeric products, cause a particularly low level of degradation of the surrounding plastic (in particular polymer degradation) when they are incorporated into plastics.

The degradation of the surrounding plastic is to be accessed on the basis of the change in specific viscosity (SV) of solutions of the polymer prior to and after processing. The higher the SV, i.e. the nearer to the value for the untreated polymer, the lower of the level of polymer degradation during the incorporation of the flame retardant.

The degradation of the surrounding plastic is also to be assessed via the melt volume index. Here, the viscosity of a polymer melt with the additive under consideration is compared with the viscosity of an untreated melt. The smaller the fall in viscosity in comparison with an untreated melt, the greater the advantage.

The invention therefore provides dialkylphosphinic salts of the formula (I)

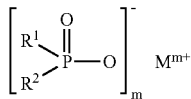

where

R$^1$, R$^2$ identical or different, are C$_1$-C$_6$-alkyl, linear or branched

M is Mg, Ca, Al, Sb, Sn, Ge, Ti, Fe, Zr, Zn, Ce, Bi, Sr, Mn, Li, Na, K and/or is a protonated nitrogen base;

m is from 1 to 4;

wherein the telomer content is from 0.01 to 6% by weight and the telomers are ethylbutylphospinic salts, butylbutylphosphinic salts, ethylhexylphosphinic salts, butylhexylphosphinic salts, and/or hexylhexylphosphinic salts.

The telomer content is preferably from 0.1 to 5% by weight.

The telomer content is particularly preferably from 0.2 to 2.5% by weight.

M is preferably aluminum, calcium, titanium, zinc, tin, or zirconium.

R$^1$ and R$^2$, identical or different, are preferably methyl, ethyl, n-propyl, isopropyl, n-butyl, isobutyl, tert-butyl, n-pentyl, isopentyl, n-hexyl, and/or isohexyl.

Preferred dialkylphosphinic salts are aluminum tris(diethylphosphinate), aluminum tris(methylethylphosphinate), titanyl bis(diethylphosphinate), titanium tetrakis(diethylphosphinate), titanyl bis(methylethylphosphinate), titanium tetrakis(methylethylphosphinate), zinc bis(diethylphosphinate), zinc bis(methylethylphosphinate), and mixtures of these.

The telomers are also preferably those from the following group: C$_2$-alkyl-C$_4$-alkylphosphinic salts, C$_4$-alkyl-C$_4$-alkylphosphinic salts, C$_2$-alkyl-C$_6$-alkylphosphinic salts, C$_4$-alkyl-C$_6$-alkylphosphinic salts, C$_6$-alkyl-C$_6$-alkylphosphinic salts.

The residual moisture level of the inventive dialkylphosphinic salts is preferably from 0.01 to 10% by weight, with preference from 0.1 to 1% by weight.

The average particle size of the inventive dialkylphosphinic salts is preferably from 0.1 to 1000 μm, particularly preferably from 50 to 500 μm, and in particular from 10 to 100 μm.

The inventive dialkylphosphinic salts have a preferred bulk density of from 80 to 800 g/l, particularly preferably from 200 to 700 g/l.

The invention also provides the use of the inventive dialkylphosphinic salts as flame retardants.

The invention also provides flame retardant compositions which comprise at least one inventive dialkylphosphinic salt.

The inventive flame retardant composition preferably comprises from 50 to 99.9% by weight of at least one inventive dialkylphosphinic salt and from 0.1 to 50% by weight of at least one additive.

The inventive flame retardant composition particularly preferably comprises from 95 to 70% by weight of at least one inventive dialkylphosphinic salt and from 5 to 30% by weight of at least one additive.

The additives preferably derive from the following group: melamine phosphate, dimelamine phosphate, pentamelamine triphosphate, trimelamine diphosphate, tetrakismelamine triphosphate, hexakismelamine pentaphosphate, melamine diphosphate, melamine tetraphosphate, melamine pyrophosphate, melamine polyphosphate, melam polyphosphate, melem polyphosphate, and/or melon polyphosphate.

Other preferred additives derived from the group of oligomeric esters of tris(hydroxyethyl) isocyanurate with aromatic polycarboxylic acids, benzoguanamine, tris(hydroxyethyl) isocyanurate, allantoin, glycoluril, melamine, melamine cyanurate, urea cyanurate, dicyandiamide, and/or guanidine.

Other preferred additives derived from the group of the zinc compounds, such as zinc oxide, zinc hydroxide, zinc oxide hydrate, zinc carbonate, zinc stannate, zinc hydroxystannate, zinc silicate, zinc phosphate, zinc borate, zinc molybdate.

Finally, other preferred additives from the group of the carbodiimides and/or (poly)isocyanates, such as carbonylbis-caprolactam, and/or styrene-acrylic polymers.

The average particle size of the flame retardant composition is preferably from 0.1 to 3000 μm, with preference from 0.1 to 1000 μm, and in particular from 1 to 100 μm.

The invention also provides a flame-retardant polymer composition comprising at least one inventive dialkylphosphinic salt or at least one inventive flame retardant composition.

The flame-retardant polymer molding composition preferably comprises from 1 to 50% by weight of at least one inventive dialkylphosphinic salt or of at least one inventive flame retardant composition, from 1 to 99% by weight of polymer or a mixture of the same,
from 0 to 60% by weight of additives, and
from 0 to 60% by weight of filler.

The flame-retardant polymer molding composition preferably comprises from 5 to 30% by weight of at least one inventive dialkylphosphinic salt or of at least one inventive flame retardant composition, from 5 to 90% by weight of polymer or a mixture of the same,
from 5 to 40% by weight of additives, and
from 5 to 40% by weight of filler.

The polymer is preferably derived from the group of the thermoplastic polymers, such as polyesters, polystyrene, or polyamide, and/or that of the thermoset polymers.

The polymer molding composition preferably has the shape of a cylinder with a circular, elliptical, or irregular base, or of a sphere, cushion, cube, parallelepiped, or prism.

The cylinder length:diameter ratio is preferably from 1:50 to 50:1, with preference from 1:5 to 5:1.

The residual moisture level in the flame-retardant polymer molding composition is preferably from 0.01 to 10% by weight, with preference 0.1 to 1% by weight.

The invention also provides a process for preparation of flame-retardant inventive polymer molding compositions, which comprises mixing the inventive dialkylphosphinic salts and/or the inventive inventive flame retardant compositions with the polymer pellets and optionally additives in a mixer, and homogenizing them in the polymer melt at relatively high temperatures in a compounding assembly, and then drawing off the homogenized polymer extrudate, cooling it, and dividing it into portions.

The compounding assembly preferably derives from the group of the single-screw extruders, multizone screws, or twin-screw extruders
Preferred processing temperatures
for polystyrene are from 170 to 200° C.,
for polypropylene are from 200 to 300° C.,
for polyethylene terephthalate (PET) are from 250 to 290° C.,
for polybutylene terephthalate (PBT) are from 230 to 270° C.,
for nylon-6 (PA 6) are from 260 to 290° C.,
for nylon-6.6 (PA 6.6) are from 260 to 290° C.,
and for polycarbonate are from 280 to 320° C.

The effective screw length (L) of the extruder (compounding assembly) as a multiple of the screw diameter (D) are preferably from 4 to 200 D, with preference from 10 to 50 D.

The invention also provides the use of the inventive dialkylphosphinic salts and/or of the inventive flame retardant compositions in flame-retardant polymer moldings.

The invention also provides flame-retardant polymer moldings, flame-retardant polymer films, flame-retardant polymer filaments, or flame-retardant polymer fibers comprising the inventive dialkylphosphinic salts and/or the inventive flame retardant composition.

The flame-retardant polymer moldings, flame-retardant polymer films, flame-retardant polymer filaments, or flame-retardant polymer fibers preferably comprise
from 1 to 50% by weight of dialkylphosphinic salts and/or the flame retardant composition,
from 1 to 99% by weight of polymer or a mixture of the same
from 0 to 60% by weight of additives
from 0 to 60% by weight of filler.

The flame-retardant polymer moldings, flame-retardant polymer films, flame-retardant polymer filaments, or flame-retardant polymer fibers particularly preferably comprise
from 5 to 30% by weight of dialkylphosphinic salts and/or the flame retardant composition,
from 5 to 90% by weight of polymer or a mixture of the same
from 5 to 40% by weight of additives
from 5 to 40% by weight of filler.

Finally, the invention also provides a process for production of flame-retardant polymer moldings, which comprises processing flame-retardant inventive polymer molding compositions via injection molding and compression molding, foam injection molding, internal gas pressure injection molding, blow molding, cast-film production, calendering, laminating, or coating at relatively high temperatures to give the flame-retardant polymer molding.

Preferred processing temperatures in this process are
for polystyrene are from 200 to 250° C.,
for polypropylene are from 200 to 300° C.,
for polyethylene terephthalate (PET) are from 250 to 290° C.,
for polybutylene terephthalate (PBT) are from 230 to 270° C.,
for nylon-6 (PA 6) are from 260 to 290° C.,
for nylon-6.6 (PA 6.6) are from 260 to 290° C.,
and for polycarbonate are from 280 to 320° C.

Among protonated nitrogen bases, preference is given to the protonated bases of ammonia, melamine, and triethanolamine, in particular $NH_4^+$. These also include the protonated bases of melamine, urea, biuret, guanidine, dodecylguanidine, allantoin, acetoguanamine, benzoguanamine, tolyltriazole, benzotriazole, 2-amino-4-methylpyrimidine, benzylurea, acetyleneurea, hydantoin, malonamide amidine, dimethylurea, diphenylguanidine, 5,5-diphenylhydantoin, N,N'-diphenylurea, ethylenebis(5-triazone), glycine anhydride, tetramethylurea, condensates of melamine, e.g. melem, melam or melon, or compounds of this type with a higher degree of condensation.

The inventive dialkylphosphinic salts have a preferred content of initiator end groups of from 0.0001 to 10 mol %, particularly preferably from 0.001 to 1 mol %. During free-radical chain termination, initiator end groups can remain bonded to the final molecule of the free-radical chain.

The preferred L color values of the inventive dialkylphosphinic salts are from 85 to 99.9, particularly preferably from 90 to 98.

The preferred a color values of the inventive dialkylphosphinic salts are from −4 to +9, particularly preferably from −2 to +6.

The preferred b color values of the inventive dialkylphosphinic salts are from −2 to +6, particularly preferably from −1 to +3.

The color values given are the Hunter system values (CIE-LAB-System, Commission Internationale d'Eclairage). L values progress from 0 (black) to 100 (white), a values from −a (green) to +a (red), and b values from −b (blue) to +b (yellow).

The preferred inventive application for the inventive dialkylphosphinic salts is as flame retardants themselves and/or in flame retardant compositions. To this end, they are preferably used together with other additives.

Examples of other preferred additives in these flame retardant compositions are synergists, as described in DE-A-28 27 867, DE-A-199 33 901, DE-A-196 14 424, or DE-A-197 34 437.

Preferred synergists used according to the invention comprise melamine phosphate (e.g. ®Melapur MP from Ciba-DSM Melapur), dimelamine phosphate, pentamelamine triphosphate, trimelamine diphosphate, tetrakismelamine triphosphate, hexakismelamine pentaphosphate, melamine diphosphate, melamine tetraphosphate, melamine pyrophosphate (e.g. ®Budit 311 from Budenheim, ®MPP-B from Sanwa Chemicals), melamine polyphosphates, melam polyphosphates, melem polyphosphates, and/or melon polyphosphates. Particular preference is given to melamine polyphosphates, such as ®Melapur 200/70 from Ciba-DSM Melapur, ®Budit 3141, 3141 CA and 3141 CB, and melamine polyphosphate/melamine pyrophosphate grades 13-1100,13-1105,13-1115, MPP02-244 from Hummel-Croton und PMP-200 from Nissan.

Other preferred synergists are melamine condensates, such as melam, melem, and/or melon.

Preferred synergists in another embodiment are condensates of melamine or the products of the melamine/phosphoric acid reaction, or products of the melamine condensate/phosphoric acid reaction, or mixtures of the products mentioned. Examples of condensates of melamine are melem, melam, or melon, or compounds of this type with higher degree of condensation, or mixtures of the same, an example of a process for preparing these being that described in WO 96/16948.

The reaction products with phosphoric acid are compounds produced via reaction melamine or of the condensed melamine compounds, such as melam, melem, or melon, etc., with phosphoric acid. Examples of these are melamine polyphosphate, melam polyphosphate, and melem polyphosphate, and mixed polysalts, e.g. as described in WO 98/39306. The compounds mentioned have been disclosed in the literature and may also be prepared via processes other than the direct reaction with phosphoric acid. By way of example, melamine polyphosphate may be prepared on the basis of WO 98/45364 via the reaction of the polyphosphoric acid and melamine, or on the basis of WO 98/08898 via condensation of melamine phosphate or melamine pyrophosphate.

Other preferred inventive synergists are oligomeric esters of tris(hydroxyethyl) isocyanurate with aromatic polycarboxylic acids, benzoguanamine, tris(hydroxyethyl) isocyanurate, allantoin, glycoluril, melamine, melamine cyanurate (e.g. ®Melapur MC or ®Melapur MC XL from Ciba-DSM Melapur), urea cyanurate, dicyandiamide, and/or guanidine.

Other preferred inventive synergists are nitrogen-containing phosphates of the formulae $(NH_4)_y H_{3-y} PO_4$ or $(NH_4 PO_3)_z$, where y is from 1 to 3 and z is from 1 to 10 000

The nitrogen compounds are preferably those of the formulae (III) to (VIII), or a mixture thereof

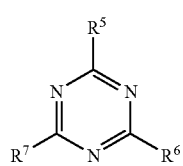

(III)

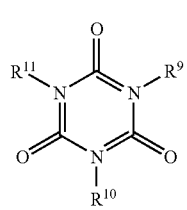

(IV)

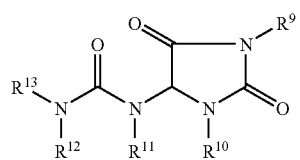

(V)

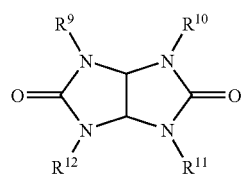

(VI)

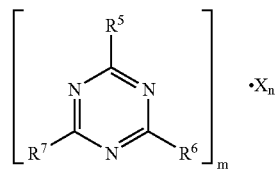

(VII)

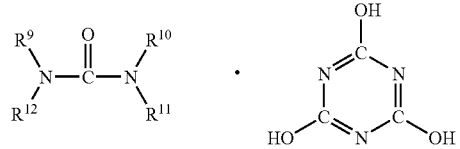

(VIII)

where
R$^5$ to R$^7$ are hydrogen, C$_1$-C$_8$-alkyl, C$_5$-C$_{16}$-cycloalkyl or -alkylcycloalkyl, possibly substituted with a hydroxy or a C$_1$-C$_4$-hydroxyalkyl function, C$_2$-C$_8$-alkenyl, C$_1$-C$_8$-alkoxy, -acyl, -acyloxy, C$_6$-C$_{12}$-aryl or -arylalkyl, —OR$^8$ or —N(R$^8$)R$^9$, including systems of acyclic-N or aromatic-N type,
R$^8$ is hydrogen, C$_1$-C$_8$-alkyl, C$_5$-C$_{16}$-cycloalkyl or -alkylcycloalkyl, possibly substituted with a hydroxy or a C$_1$-C$_4$-hydroxyalkyl function, C$_2$-C$_8$-alkenyl, C$_1$-C$_8$-alkoxy, -acyl, -acyloxy or C$_6$-C$_{12}$-aryl or -arylalkyl,
R$^9$ to R$^{13}$ are as defined for R$^8$ or —O—R$^8$,
m and n independently of one another, are 1, 2, 3, or 4,
x is acids which can form adducts with triazine compounds (III).

Other preferred additives in the inventive flame retardant compositions are, as in EP-A-1 024 167, by way of example, oxygen compounds of silicon, magnesium compounds, metal carbonates of metals of the second main group of the Periodic Table, red phosphorus, zinc compounds, or aluminum compounds.

Other preferred additives in the inventive flame retardant compositions are oxides, hydroxides, carbonates, silicates, borates, stannates, mixed oxide hydroxides, oxide hydroxide carbonates, hydroxide silicates, or hydroxide borates, or a mixture of these substances.

Other preferred additives in the inventive flame retardant compositions are magnesium compounds, e.g. magnesium oxide, magnesium hydroxide, hydrotalcites, dihydrotalcite, magnesium carbonates, or magnesium calcium carbonates.

Other preferred additives in the inventive flame retardant compositions are calcium compounds, e.g. calcium hydroxide, calcium oxide, hydrocalumite.

Other preferred additives in the inventive flame retardant compositions are zinc compounds, e.g. zinc oxide (e.g. activated zinc oxide), zinc hydroxide, zinc oxide hydrate, zinc carbonate (e.g. basic zinc carbonate, anhydrous zinc carbonate), zinc stannate, zinc hydroxystannate, basic zinc silicate, basic zinc phosphate, basic zinc borate (e.g. Firebrake ZB, 415, 500 from Borax), basic zinc molybdates (Kemgard 911B, Kemgard 911C from Sherwin-Williams Company), or basic zinc sulfides.

Other preferred additives in the inventive flame retardant compositions are aluminum compounds, e.g. aluminum oxide, aluminum hydroxide, boeagmite, gibbsite, or aluminum phosphate.

Other preferred additives in the inventive flame retardant compositions are manganese compounds, e.g. manganese oxide, manganese hydroxide.

Other preferred additives in the inventive flame retardant compositions are tin compounds, e.g. tin oxide.

Other preferred additives in the inventive flame retardant compositions are described in DE-A-199 20 276 (BASF), e.g. from the carbodiimides groups (e.g. ®Stabaxol P from BASF), and/or (poly)isocyanates (e.g. ®Basonat HI 100 or ®Vestanat T 1890/100).

Other preferred additives in the inventive flame retardant compositions are carbonylbiscaprolactam (Allinco) or styrene-acrylic polymers (®Joncryl ADR-4357 from Johnson).

Other preferred additives in the inventive flame retardant composition come from the group of the sterically hindered phenols (e.g. Hostanox OSP 1), sterically hindered amines, and light stabilizers (e.g. Chimasorb 944, Hostavin grades), phosphonites, and antioxidants (e.g. Sandostab® P-EPQ from Clariant), and release agents (Licomont grades from Clariant).

The inventive dialkylphosphinic salts are preferably used in compounded form in flame retardant compositions. The inventive forms may have been treated by coating or in order to reduce dusting, or by compacting, melt pelletization, droplet pelletization, dispersion, or spray pelletization.

The average particle size of the inventive flame retardant composition is from 0.1 to 3000 μm.

In one embodiment, the average particle size of the inventive flame retardant composition is from 0.1 to 1000 μm, preferably from 1 to 100 μm.

In another embodiment, the average particle size of the inventive flame retardant composition is from 100 to 3000 μm, preferably from 200 to 2000 μm.

The bulk density of the inventive flame retardant composition is from 80 to 1500 g/l, particularly preferably from 200 to 1000 g/l.

In another embodiment, the preferred bulk density of the inventive flame retardant compositions is from 80 to 800 g/l, particularly preferably from 200 to 700 g/l.

In another embodiment, the preferred bulk density of the inventive flame retardant compositions is from 200 to 1500 g/l, preferably from 300 to 1000 g/l.

The invention in particular provides the use of the inventive dialkylphosphinic salts in flame-retardant polymer molding compositions comprising polymer. Preferred polymers of the invention are thermoplastic and/or thermoset polymers.

Thermoset and thermoplastic polymers may be used in the invention.

The polymers are polymers of mono- and diolefins, for example polypropylene, polyisobutylene, poly-1-butene, poly-4-methyl-1-pentene, polyisoprene, or polybutadiene, or polymers of cycloolefins, e.g. of cyclopentene or norbornene; or polyethylene (if appropriate crosslinked), e.g. high-density polyethylene (HDPE), high-density high-molecular-weight polyethylene (HDHMWPE), high-density ultrahigh-molecular-weight polyethylene (HDUHMWPE), medium-density polyethylene (MDPE), low-density polyethylene (LDPE), linear low-density polyethylene (LLDPE), branched low-density polyethylene (VLDPE), or else a mixture of these.

The polymers are preferably copolymers of mono- and diolefins with one another or with other or with other vinyl monomers, e.g. ethylene-propylene copolymers, linear low-density polyethylene (LLDPE), or a mixture of this with low-density polyethylene (LDPE), or are propylene-1-butene copolymers, propylene-isobutylene copolymers, ethylene-1-butene copolymers, ethylene-hexene copolymers, propylene-butadiene copolymers, isobutylene-isoprene copolymers, ethylene-alkyl acrylate copolymers, ethylene-alkyl methacrylate copolymers, ethylene-vinyl acetate-copolymers, or their copolymers with carbon monoxide, or ethylene-acrylic acid copolymers or their salts (ionomers), or else terpolymers of ethylene with propylene and with a diene, such as hexadiene, dicyclopentadiene, or ethylidenenorborne; or else mixtures of these copolymers with one another, e.g. polypropylene/ethylenepropylene copolymers, LDPE/ethylene-vinyl acetate copolymers, LDPE/ethylene-acrylic acid copolymers, LLDPE/ethylene-vinyl acetate copolymers, LLDPE/ethylene-acrylic acid copolymers, or alternating or random polyalkylene/carbon monoxide copolymers, or their mixtures with other polymers, e.g. with polyamides.

The polymers are preferably hydrocarbon resins (e.g. C5-C9), inclusive of hydrogenated modifications thereof (e.g. tackifier resins), or a mixture of polyalkylenes and starch.

Other preferred polymers are polystyrene (Polystyrol 143E (polystyrene 143E (BASF), poly(p-methylstyrene), poly-(alpha-methylstyrene)).

Other preferred polymers are copolymers of styrene or alpha-methylstyrene with dienes or with acrylic derivatives, e.g. styrene-butadiene, styrene-acrylonitrile, styrene-alkyl methacrylate, styrene-butadiene-alkyl acrylate, and styrene-butadiene-alkyl methacrylate, styrene-maleic anhydride, styrene-acrylonitrile-methyl acrylate; mixtures of high impact resistance composed of styrene copolymers and of another polymer, e.g. of a polyacrylate, of a diene polymer, or of an ethylene-propylene-diene terpolymer; or else block copolymers of styrene, e.g. styrene-butadiene-styrene, styrene-isoprene-styrene, styrene-ethylene/butylene-styrene, or styrene-ethylene/propylene-styrene.

Other preferred polymers are graft copolymers of styrene or alpha-methylstyrene, e.g. styrene on polybutadiene, styrene on polybutadiene-styrene copolymers or on polybutadiene-acrylonitrile copolymers, styrene and acrylonitrile (or methacrylonitrile) on polybutadiene; styrene, acrylonitrile, and methyl methacrylate on polybutadiene; styrene and maleic anhydride on polybutadiene; styrene, acrylonitrile, and maleic anhydride or maleimide on polybutadiene; styrene and maleimide on polybutadiene, styrene and alkyl acrylates or alkyl methacrylates on polybutadiene, styrene and acrylonitrile on ethylene-propylene-diene terpolymers, styrene and acrylonitrile on polyalkyl acrylates or on polyalkyl methacrylates, styrene and acrylonitrile on
acrylate-butadiene copolymers, or else a mixture of these, e.g. those known as ABS polymers, MBS polymers, ASA polymers, or AES polymers.

Other preferred polymers are halogen-containing polymers, e.g. polychloroprene, chlorinated rubber, chlorinated and brominated copolymer derived from isobutylene-isoprene (halobutyl rubber), chlorinated or chlorosulfonated polyethylene, copolymers of ethylene and of chlorinated ethylene, epichlorohydrinhomopolymers, epichlorohydrincopolymers, and in particular polymers derived from halogen-containing vinyl compounds, e.g. polyvinyl chloride, polyvinylidene chloride, polyvinyl fluoride, polyvinylidene fluoride; or else copolymers of these, e.g. vinyl chloride-vinylidene chloride, vinyl chloride-vinyl acetate, or vinylidene chloride-vinyl acetate.

The preferred polymers are polymers which derive from alpha-beta-unsaturated acids and from their derivatives, e.g. polyacrylates and polymethacrylates, butyl-acrylate-impact-modified polymethyl methacrylates, polyacrylamides, and polyacrylonitriles, and copolymers of the monomers mentioned with one another or with other unsaturated monomers, e.g. acrylonitrile-butadiene copolymers, acrylonitrile-alkyl acrylate copolymers, acrylonitrile-alkoxyalkyl acrylate copolymers, acrylonitrile-vinyl halide copolymers, or acrylonitrile-alkyl methacrylate-butadiene terpolymers.

Other preferred polymers are polymers which derive from unsaturated alcohols and amines or from their acyl derivatives or from their acetals, e.g. polyvinyl alcohol, polyvinyl acetate, stearate, benzoate, maleate, polyvinyl butyral, polyallyl phthalate, polyallylmelamine; and also their copolymers with olefins.

Other preferred polymers are homo- and copolymers of cyclic ethers, e.g. polyalkylene glycols, polyethylene oxide, polypropylene oxide, or their copolymers with bisglycidyl ethers.

Other preferred polymers are polyacetals, such as polyoxymethylene, and also those polyoxymethylenes which contain comonomers, e.g. ethylene oxide; and polyacetals modified by thermoplastic polyurethanes, modified by acrylates, or modified by MBS.

Other preferred polymers are polyphenylene oxides and polyphenylene sulfides, and their mixtures with styrene polymers or with polyamides.

Other preferred polymers are polyurethanes which derive on the one hand from polyethers, from polyesters, or from polybutadienes having terminal hydroxy groups and on the other hand from aliphatic or aromatic polyisocyanates, preference also being given to precursors of these.

Other preferred polymers are polyamides and copolyamides which derive from diamines and from dicarboxylic acids, and/or from aminocarboxylic acids, or from the corresponding lactams, e.g. nylon-2,12, nylon-4 (poly-4-aminobutyric acid, DuPont), nylon-4,6 (poly(tetramethyleneadipamide, DuPont), nylon-6 (polycaprolactam, poly-6-aminohexanoic acid, DuPont, Akulon K122, DSM; Zytel 7301, DuPont; Durethan B 29, Bayer), nylon-6,6 (poly(N,N'-hexamethyleneadipamid), DuPont, Zytel 101, DuPont; Durethan A30, Durethan AKV, Durethan AM, Bayer; Ultramid A3, BASF), nylon-6,9 (poly(hexamethylenenonanediamide), DuPont), nylon-6,10 (poly(hexamethylenesebacamids), DuPont), nylon-6,12 (poly(hexamethylenedodecanediamide), DuPont), nylon-6/6,6 (poly(hexamethyleneadipamide-cocaprolactam), DuPont), nylon-7 (poly-7-aminoheptanoic acid, DuPont), nylon-7,7 (polyheptamethylenepimelamide, DuPont), nylon-8 (poly-8-aminooctanoic acid, DuPont), nylon-8,8 (polyoctamethylenesuberamide, DuPont), nylon-9 (poly-9-aminononanoic acid, DuPont), nylon-9,9 (polynonamethyleneazelamide, DuPont), nylon-10 (poly-10-aminodecanoic acid, DuPont), nylon-1 0,9 (poly(decamethyleneazelamide), DuPont), nylon-10,10 (polydecamethylenesebacamide, DuPont), nylon-11 (poly-11-aminoundecanoic acid, DuPont), nylon-12 (polylauryllactam, DuPont, Grillamid L20, Ems Chemie), aromatic polyamides derived from m-xylene, diamine, and adipic acid; polyamides prepared from hexamethylenediamine and iso- and/or terephthalic acid (polyhexamethyleneisophthalamide or polyhexamethyleneterephthalamide), and, if appropriate, from an elastomer as modifier, e.g. poly-2,4,4-trimethylhexamethyleneterephthalamide or poly-m-phenyleneisophthalamide; block copolymers of the abovementioned polyamides with polyolefins, with olefin copolymers, with ionomers, or with chemically bonded or grafted elastomers; or with polyethers, e.g. with polyethylene glycol, polypropylene glycol, or polytetramethylene glycol; or else copolyamides or polyamides modified by EPDM or modified by ABS; or else polyamides condensed during processing ("RIM polyamide systems").

Other preferred polymers are polyureas, polyimides, polyamideimides, polyetherimides, polyesterimides, polyhydantoins, and polybenzimidazoles.

Other preferred polymers are polyesters which derived from dicarboxylic acids and from dialcohols, and/or from hydroxycarboxylic acids, or from the corresponding lactones, e.g. polyethylene terephthalate, polybutylene terephthalate (Celanex 2500, Celanex 2002, Celanese; Ultradur, BASF), poly(1,4-dimethylolcyclohexane terephthalate), polyhydroxybenzoates, and also block polyetheresters which derive from polyethers having hydroxy end groups; and also polyesters modified by polycarbonates or modified by MBS.

Other preferred polymers are polycarbonates and polyester carbonates.

Other preferred polymers are polysulfones, polyether sulfones, and polyether ketones.

Other preferred polymers are crosslinked polymers which derive from aldehydes on the one hand and from phenols, urea or melamine on the other hand, e.g. phenol-formaldehyde resins, urea-formaldehyde resins, and melamine-formaldehyde resins.

Other preferred polymers are drying and non-drying alkyd resins.

Other preferred polymers are unsaturated polyester resins which derived from copolyesters of saturated or of unsaturated dicarboxylic acids with polyhydric alcohols, and also from vinyl compounds as crosslinking agents, the halogen-containing, flame-retardant modifications of these also being preferred.

Other preferred polymers are crosslinkable acrylic resins which derive from substituted acrylic esters, e.g. from epoxy acrylates, from urethane acrylates, or from polyester acrylates.

Other preferred polymers are alkyd resins, polyester resins, and acrylate resins which have been crosslinked by melamine resins, by urea resins, by isocyanates, by isocyanurates, by polyisocyanates, or by epoxy resins.

Other preferred polymers are crosslinked epoxy resins which derive from aliphatic, cycloaliphatic, heterocyclic, or aromatic glycidyl compounds, e.g. products of bisphenol A diglycidyl ethers, or of bisphenol F diglycidyl ethers, which are crosslinked by means of conventional hardeners, e.g. by means of an anhydrides or of amines, with or without accelerators.

Other preferred polymers are mixtures (polyblends) of the abovementioned polymers, e.g. PP/EPDM, polyamide/EPDM, or ABS, PVC/EVA, PVC/ABS, PVC/MBS, PC/ABS, PBTP/ABS, PC/ASA, PC/PBT, PVC/CPE, PVC/acrylates, POM/thermoplastic PU, PC/thermoplastic PU, POM/acrylate, POM/MBS, PPO/HIPS, PPO/PA 6.6, and copolymers, PA/HDPE, PA/PP, PA/PPO, PBT/PC/ABS, or PBT/PET/PC.

Compounding assemblies which may be used in the invention are single-screw extruders, e.g. from Berstorff GmbH, Hanover, or from Leistritz, Nuremberg.

Other compounding assemblies which may be used in the invention are multizone screw extruders with three-section screws and/or short-compression-section screws.

Other compounding assemblies which may be used in the invention are co-kneaders, e.g. from Coperion Buss Compounding Systems, Pratteln, Switzerland, e.g. MDK/E46-11 D, and/or laboratory kneaders (MDK 46 from Buss, Switzerland with L=11 D).

Other compounding assemblies which may be used in the invention are twin-screw extruders, e.g. from Coperion Werner & Pfleiderer GmbH & Co. KG, Stuttgart (ZSK 25, ZSK30, ZSK 40, ZSK 58, ZSK MEGAcompounder 40, 50, 58, 70, 92, 119, 177, 250, 320, 350, 380), and/or from Berstorff GmbH, Hanover, or Leistritz Extrusionstechnik GmbH, Nuremberg.

Other compounding assemblies which may be used in the invention are ring extruders, e.g. from 3+Extruder GmbH, Laufen, with a ring of from three to twelve small screws which rotate around a static core, and/or planetary-gear extruders, e.g. from Entex, Bochum, and/or vented extruders, and/or cascade extruders, and/or Maillefer screws.

Other compound assemblies which may be used in the invention are compounders with counter-rotating twin screws, e.g. Compex 37 or Compex 70 from Krauss-Maffei Berstorff.

Effective screw lengths for the invention from 20 to 40 D in the case of single-screw extruders.

Effective screw lengths (L) in the invention in the case of multizone-screw extruders are 25 D with feed section (L=10 D), transition section (L=6 D), metering section (L=9 D).

Effective screw lengths in the invention in the case of twin-screw extruders are from 8 to 48 D.

The preferred form of the flame-retardant polymer molding composition is pellet (compounded) form. The shape of the pellets is preferably that of a cylinder with a circular, elliptical, or irregular base, or of a sphere, cushion, cube, parallelepiped, or prism.

The length:diameter ratio of the pellets is preferably from 1:50 to 50:1, with preference from 1:5 to 5:1.

The diameter of the pellets is preferably from 0.5 to 15 mm, particularly preferably from 2 to 3 mm, and their length is preferably from 0.5 to 15 mm, particularly preferably from 2 to 5 mm. The pellets obtained are, by way of example, dried at 90° C. for 10 h in an oven with air circulation.

Inventive SV numbers of inventive flame-retardant polymer molding compositions based on polybutylene terephthalate are from 800 to 1400, preferably from 900 to 1300, and particularly preferably from 1000 to 1200.

Inventive melt volume indices of inventive flame-retardant polymer molding compositions based on polyamide are from 0 to 15, preferably from 3 to 12.

The invention then uses the inventive flame-retardant polymer molding compositions to produce polymer moldings.

The inventive flame-retardant polymer molding compositions are suitable for production of fibers, films, or moldings, in particular for uses in the electrical and electronic sectors.

The invention gives preference to the use of the inventive flame-retardant polymer moldings as lamp parts, such as lamp sockets and lamp holders, plugs and multipoint connectors, coil formers, casings for capacitors or connectors, and circuit-breakers, relay housings, and reflectors.

Melt Volume Index

The flowability of the molding compositions was determined via determination of the melt volume index (MVR) 275° C./2.16 kg. A marked rise in the MVR value indicates polymer degradation.

Determination of SV Number (Specific Viscosity)

Specific viscosity (SV value) is a dimensionless property permitting assessment of compatibility of an additive in a polymer formulation. This is derived from determination of the viscosity of a solution of the polymer in a solvent. The ratio between the viscosity of the polymer solution and the viscosity of the pure solvent is calculated.

0.5 g of the polymer specimen (PBT, for example) were weighed out with 50 ml of dichloroacetic acid (S) into a 250 ml Erlenmeyer flask with ground-glass stopper. The specimen was dissolved over a period of 16 h at 25° C., with stirring. The solution is filtered through a G1 glass frit. 20 ml of the solution were charged to the capillary, suspended in the (Ubbelohde) capillary viscometer, and temperature-controlled to 25° C. The SV value is calculated from the following formula:

SV value=100*[flow time (specimen solution)/flow time (S)-1].

A mixture of phenol and 1,2-dichlorobenzene (1:1, w/w) or m-cresol may also be used instead of dichloroacetic acid for polyethylene terephthalate and polybutylene terephthalate. For polyamide, use may be made of sulfuric acid, formic acid, or m-cresol.

Production, Processing, and Testing of Flame-Retardant Plastics Molding Compositions and Plastics Moldings The flame retardant components were mixed with the polymer pellets and optionally with additives, and incorporated in a twin-screw extruder (Leistritz LSM 30/34) at temperatures of from 230 to 260° C. (GRPBT) or from 260 to 280° C. (GRPA 66). The homogenized polymer extrudate was drawn off, cooled in a water bath, and then palletized.

After solution drying, the molding compositions were processed in an injection molding machine (Aarburg Allrounder) at melt temperatures of from 240 to 270° C. (GRPBT) or from 260 to 290° C. (GRPA 66) to give test specimens.

The UL 94 (Underwriters Laboratories) fire plastication was determined on test specimens from each mixture, using test specimens of thickness 1.5 mm.

The following fire classifications are given by UL 94:

V-0: afterflame time never longer than 10 seconds, total of afterflame times for 10 flame applications not more than 50 seconds, no flaming drops, no complete consumption of the specimen, afterglow time for the specimen never longer than 30 seconds after end of flame applications V-1: afterflame time never longer than 30 seconds after end of flame application, total of afterflame times for end flame applications not more than 250 seconds, afterglow time for the specimens never longer than 60 seconds after end of flame application, other criteria as for V-0

V-2: cotton indicator ignited by flaming drops; other criteria as for V-1 not classifiable (ncl): does not comply with fire classification V-2.

The examples below provide further illustration of the invention.

EXAMPLE 1 COMPARISON

An aluminum dialkylphosphinate was first prepared. For this, 2.2 kg (20.7 mol) of sodium hypophosphite monohydrate were dissolved in 8 kg (7.62 l) of acetic acid and charged to a 16 l jacketed pressure reactor made from enameled steel. Once the reaction mixture had been heated to 85° C., ethylene was introduced by way of a reducing valve set to 5 bar until saturation had been reached in the reactor. The reaction was initiated, with continuous stirring, via feed of a solution of 56 g (1 mol %) of 2,2'-azobis(2-amidinopropane) dihydrochloride in 250 ml of water, and the reaction was controlled by way of the free-radical-initiator feed rate in such a way as to keep the reaction temperature in the reactor at 95° C. or below with a jacket temperature of 80° C., with continuous feed of ethylene at an average pressure of about 5 bar. The total feed time was 3 hours. The mixture was then allowed to continue reaction at 85° C. for a further 3 h. The reactor was depressurized and cooled to room temperature. The total weight of product was 11.7 kg. This corresponds to 1.2 kg of ethylene take-up (100% of theory).

800 g of the resultant mixture composed mainly of sodium diethylphosphinate were dissolved in 2500 ml of acetic acid, and 38 g (0.48 mol) of aluminum hydroxide were then added. The mixture was then heated at reflux for about 4 hours, cooled, and filtered. The resultant solid was washed first with 1 liter of glacial acetic acid, then with 1 liter of distilled water, and finally with 500 ml of acetone, and then dried in vacuo at 130° C.

The constitution of the product is as follows:
aluminum diethylphosphinate: 87.2 mol %
aluminum ethylbutylphosphinate: 11.9 mol %
aluminum ethylphosphonate: 0.9 mol %
residual acetate: 0.88% by weight

EXAMPLE 2 COMPARISON

An aluminum dialkylphosphinate was first prepared. For this, a mixture of 2.64 kg (20 mol) of a 50% strength aqueous solution of hypophosphorous acid and 7 kg of acetic acid was charged to a 16 l jacketed pressure reactor made from enameled steel. Once the reaction mixture had been heated to 100° C., ethylene was introduced by way of a reducing valve set to 5 bar until saturation had been reached in the reactor. A solution of 56 g of 2,2'-azobis(N,N'-dimethyleneisobutyramidine) dihydrochloride in 500 g of acetic acid was fed uniformly into the mixture over a period of 6 h, with continuous stirring, using an ethylene pressure of 5 bar at a temperature of from 100-105° C. The solution obtained after a further reaction time of 1 h, depressurization of the reactor, and cooling to room temperature was very substantially freed from the acetic acid solvent on a rotary evaporator, and then treated with 10 l of water. Within a period of one hour, 4500 g (3.5 mol) of a 46% strength aqueous solution of $Al_2(SO_4)_3$ 14 $H_2O$ were added. The resultant solid was then filtered, washed twice with water, on each occasion using 2 l, and dried in vacuo at 130° C.

The constitution of the product is as follows:
aluminum diethylphosphinate: 90.8 mol %
aluminum ethylbutylphosphinate: 8.4 mol %
aluminum ethylphosphonate: 0.8 mol %
residual acetate: 0.45% by weight

EXAMPLE 3

An aluminum dialkylphosphinate was first prepared. For this, 1500 g (14 mol) of sodium hypophosphite monohydrate were dissolved in 7.5 kg of water and charged to a 16 l jacketed pressure reactor made from enameled steel. Once the reaction mixture had been heated to 100° C., ethylene was introduced by way of a reducing valve set to 6 bar until saturation had been reached in the reactor. A solution of 17 g (0.5 mol %) of sodium peroxodisulfate in 300 g of water was fed uniformly into the mixture over a period of 6 h, with continuous stirred, using an ethylene pressure of 6 bar and a temperature of from 100 to 110° C. After a further reaction time of 1 h, depressurization of the reactor, and cooling to about 90° C., 3000 g (4.67 mol of aluminum) a 46% strength aqueous solution of $Al_2(SO_4)_3$ 14 $H_2O$ was added within a period of 60 min. The resultant solid was then filtered off, washed with 2 l of hot water, and dried in vacuo at 130° C.

The constitution of the product is as follows:
aluminum diethylphosphinate: 98.6 mol %
aluminum ethylbutylphosphinate: 0.9 mol %
aluminum ethylphosphonate: 0.5 mol %
residual acetate: 0% by weight

EXAMPLE 4

As in Example 3, an aluminum dialkylphosphinate is first prepared.

The constitution of the product is as follows:
aluminum diethylphosphinate: 96.5 mol %
aluminum ethylbutylphosphinate: 2.7 mol %
aluminum ethylphosphonate: 0.8 mol %
residual acetate: 0% by weight

EXAMPLE 5

An aluminum dialkylphosphinate was first prepared. For this, 1500 g (14 mol) of sodium hypophosphite monohydrate were dissolved in 7.5 kg of water and charged to a 16 l jacketed pressure reactor made from enameled steel. Once the reaction mixture had been heated to 100° C., ethylene was introduced by way of a reducing valve set to 20 bar until saturation had been reached in the reactor. A solution of 32 g (1 mol %) of ammonium peroxodisulfate in 300 g of water was fed uniformly into the mixture over a period of 6 h, with continuous stirred, using an ethylene pressure of 20 bar and a temperature of from 100 to 110° C. After a further reaction time of 1 h, depressurization of the reactor, and cooling to about 90° C., 3000 g (4.67 mol of aluminum) a 46% strength aqueous solution of $Al_2(SO_4)_3$ 14 $H_2O$ was added within a period of 60 min. The resultant solid was then filtered off, washed with 2 l of hot water, and dried in vacuo at 130° C.

The constitution of the product is as follows:
aluminum diethylphosphinate: 93.9 mol %
aluminum ethylbutylphosphinate: 5.5 mol %
aluminum ethylphosphonate: 0.6 mol %
residual acetate: 0% by weight

EXAMPLE 6

A mixture composed of 100% by weight of polybutylene terephthalate 1 is compounded in a twin-screw extruder at from 230 to 260° C. as in the general specification "production, processing, and testing of flame-retardant plastics molding compositions and plastics moldings", to give a polymer molding composition. After drying, the molding compositions are processed in an injection molding machine at melt temperatures of from 240 to 270° C. to give polymer moldings. The viscosity number determined is 1072. The test specimen is not classifiable to UL 94.

EXAMPLE 7

A mixture composed of 25% by weight of product from Example 1 and 75% by weight of polybutylene terephthalate 1 is compounded in a twin-screw extruder at from 230 to 260° C. as in the general specification "production, processing, and testing of flame-retardant plastics molding compositions and plastics moldings", to give a flame-retardant polymer molding composition. After drying, the molding compositions are processed in an injection molding machine at melt temperatures of from 240 to 270° C. to give flame-retardant polymer moldings. The viscosity number determined is 719. The UL 94 classification of the test specimen is V-2.

EXAMPLE 8

A mixture composed of 25% by weight of product from Example 2 and 75% by weight of polybutylene terephthalate 1 is compounded in a twin-screw extruder at from 230 to 260° C. as in the general specification "production, processing, and testing of flame-retardant plastics molding compositions and plastics moldings", to give a flame-retardant polymer molding composition. After drying, the molding compositions are processed in an injection molding machine at melt temperatures of from 240 to 270° C. to give flame-retardant polymer moldings. The viscosity number determined is 758. The UL 94 classification of the test specimen is V-2.

EXAMPLE 9

A mixture composed of 25% by weight of product from Example 3 and 75% by weight of polybutylene terephthalate 1 is compounded in a twin-screw extruder at from 230 to 260° C. as in the general specification "production, processing, and testing of flame-retardant plastics molding compositions and plastics moldings", to give a flame-retardant polymer molding composition. After drying, the molding compositions are processed in an injection molding machine at melt temperatures of from 240 to 270° C. to give flame-retardant polymer moldings. The viscosity number determined is 1023. The UL 94 classification of the test specimen is V-0.

EXAMPLE 10

A mixture composed of 25% by weight of product from Example 4 and 75% by weight of polybutylene terephthalate 1 is compounded in a twin-screw extruder at from 230 to 260° C. as in the general specification "production, processing, and testing of flame-retardant plastics molding compositions and plastics moldings", to give a flame-retardant polymer molding composition. After drying, the molding compositions are processed in an injection molding machine at melt temperatures of from 240 to 270° C. to give flame-retardant polymer moldings. The viscosity number determined is 1034. The UL 94 classification of the test specimen is V-0.

EXAMPLE 11

A mixture composed of 25% by weight of product from Example 5 and 75% by weight of polybutylene terephthalate 1 is compounded in a twin-screw extruder at from 230 to 260° C. as in the general specification "production, processing, and testing of flame-retardant plastics molding compositions and plastics moldings", to give a flame-retardant polymer molding composition. After drying, the molding compositions are processed in an injection molding machine at melt temperatures of from 240 to 270° C. to give flame-retardant polymer moldings. The viscosity number determined is 995. The UL 94 classification of the test specimen is V-0.

EXAMPLE 12

A mixture composed of 12% by weight of product from Example 1, 6% by weight of melamine cyanurate, 52% by weight of polybutylene terephthalate 2, and 30% by weight of glass fibers 1 are compounded in a twin-screw extruder at from 230 to 260° C. as in the general specification "production, processing, and testing of flame-retardant plastics molding compositions and plastics moldings", to give a flame-retardant polymer molding composition. After drying, the molding compositions are processed in an injection molding machine at melt temperatures of from 240 to 270° C. to give flame-retardant polymer moldings. The viscosity number determined is 716. The UL 94 classification of the test specimen is V-1.

EXAMPLE 13

A mixture composed of a mixture of 12% by weight of product from Example 3, 6% by weight of melamine cyanurate, 52% by weight of polybutylene terephthalate 2, and 30% by weight of glass fibers 1 were compounded in a twin-screw extruder at from 230 to 260° C. as in the general specification "production, processing, and testing of flame-retardant plastics molding compositions and plastics moldings", to give a flame-retardant polymer molding composition. After drying, the molding compositions are processed in an injection molding machine at melt temperatures of from 240 to 270° C. to give flame-retardant polymer moldings. The viscosity number determined is 1005. The UL 94 classification of the test specimen is V-0.

EXAMPLE 14

A mixture composed of 70% by weight of nylon-6,6 and 30% by weight of glass fibers 1 is compounded in a twin-screw extruder at from 260 to 280° C. as in the general specification "production, processing, and testing of flame-retardant plastics molding compositions and plastics moldings", to give a polymer molding composition. After drying, the molding compositions are processed in an injection molding machine at melt temperatures of from 260 to 290° C. to give polymer moldings. The melt volume index determined is 5.8 $cm^3/min$.

EXAMPLE 15 COMPARISON

A mixture composed of 11.4% by weight of product from Example 1, 5.7% by weight of melamine polyphosphate, 0.9% by weight of zinc borate, 52% by weight of nylon-6,6, and 30% by weight of glass fibers 1 are compounded in a twin-screw extruder at from 260 to 280° C. as in the general specification "production, processing, and testing of flame-retardant plastics molding compositions and plastics moldings", to give a polymer molding composition. After drying, the molding compositions are processed in an injection molding machine at melt temperatures of from 260 to 290° C. to give polymer moldings. The melt volume index determined is 16.7 $cm^3/min$. The UL 94 plastication of the test specimen is V-2.

EXAMPLE 16

A mixture composed of 11.4% by weight of products from Example 3, 5.7% by weight of melamine polyphosphate, 0.9% by weight of zinc borate, 52% by weight of nylon-6,6, and 30% by weight of glass fibers 1 are compounded in a twin-screw extruder at from 260 to 280° C. as in the general specification "production, processing, and testing of flame-retardant plastics molding compositions and plastics moldings", to give a polymer molding composition. After drying, the molding compositions are processed in an injection molding machine at melt temperatures of from 260 to 290° C. to give polymer moldings. The melt volume index determined is 4.1 $cm^3/min$. The UL 94 classification of the test specimen is V-0.

EXAMPLE 17

A mixture composed of 11.4% by weight of product from Example 4, 5.7% by weight of melamine polyphosphate, 0.9% by weight of zinc oxide, 52% by weight of nylon-6,6, and 30% by weight of glass fibers 1 are compounded in a twin-screw extruder at from 260 to 280° C. as in the general specification "production, processing, and testing of flame-retardant plastics molding compositions and plastics moldings", to give a polymer molding composition. After drying, the molding compositions are processed in an injection molding machine at melt temperatures of from 260 to 290° C. to give polymer moldings. The melt volume index determined is 5.6 cm$^3$/min. The UL 94 classification of the test specimen is V-0.

EXAMPLE 18

A mixture composed of 12% by weight of product from Example 4, 6% by weight of melamine polyphosphate, 52% by weight of nylon-6, and 30% by weight of glass fibers 2 are compounded in a twin-screw extruder at from 260 to 280° C. as in the general specification "production, processing, and testing of flame-retardant plastics molding compositions and plastics moldings", to give a polymer molding composition. After drying, the molding compositions are processed in an injection molding machine at melt temperatures of from 260 to 290° C. to give polymer moldings. The melt volume index determined is 4.9 cm$^3$/min. The UL 94 classification of the test specimen is V-0.

EXAMPLE 19

A mixture composed of 30% by weight of product from Example 4, and 70% by weight of polystyrene are compounded in a twin-screw extruder at 170° C. as in the general specification "production, processing, and testing of flame-retardant plastics molding compositions and plastics moldings", to give a polymer molding composition. After drying, the molding compositions are processed in an injection molding machine at melt temperatures of from 200 to 250° C. to give polymer moldings. The UL 94 classification of the test specimen is V-0.

Chemicals Used

| | |
|---|---|
| Melamine polyphosphate | Melapur 200/70, Ciba SC |
| Melamine cyanurate | Melapur MC, Ciba SC |
| Zinc borate | Firebrake 500, Borax |
| Zinc oxide | Rheinchemie |
| Polybutylene terephthalate 1 | Celanex 2300 GV1/30, Celanese, USA |
| Polybutylene terephthalate 2 | Celanex 2500, Celanese, USA |
| Nylon-6,6 | Ultramid A3, BASF |
| Nylon-6 | Zytel 7301, DuPont |
| Polystyrene | Polystyrene 143 E, BASF |
| Glass fibers 1 | Vetrotex EC 10 983, 4.5 mm, Saint Gobain |
| Glass fibers 2 | Chop Vantage 3540, PPG |

TABLE 1

| | | Example | | | | |
|---|---|---|---|---|---|---|
| | | 1 (comp.) | 2 (comp.) | 3 | 4 | 5 |
| Al salt of diethylphosphinic acid | mol % | 87.2 | 90.8 | 98.6 | 96.5 | 93.9 |
| Al salt of ethylbutylphosphinic acid | mol % | 11.9 | 8.4 | 0.9 | 2.7 | 5.5 |
| Al salt of ethylphosphonic acid | mol % | 0.9 | 0.8 | 0.5 | 0.8 | 0.6 |
| Residual acetate | % by wt | 0.88 | 0.45 | 0 | 0 | 0 |

TABLE 2

| | | Example | | | | | | | | | | | | | |
|---|---|---|---|---|---|---|---|---|---|---|---|---|---|---|---|
| | | 6 | 7 | 8 | 9 | 10 | 11 | 12 | 13 | 14 | 15 | 16 | 17 | 18 | 19 |
| Product from Example 1 | % by weight | | 25 | | | | | 12 | | | 11.4 | | | | |
| Product from Example 2 | % by weight | | | 25 | | | | | | | | | | | |
| Product from Example 3 | % by weight | | | | 25 | | | | 12 | | | 11.4 | | | |
| Product from Example 4 | % by weight | | | | | 25 | | | | | | | 11.4 | 12 | 30 |
| Product from Example 5 | % by weight | | | | | | 25 | | | | | | | | |
| Melamine polyphosphate | % by weight | | | | | | | | | | 5.7 | 5.7 | 5.7 | 6 | |
| Melamine cyanurate | % by weight | | | | | | | 6 | 6 | | | | | | |
| Zinc borate | % by weight | | | | | | | | | | 0.9 | 0.9 | 0.9 | | |
| Zinc oxide | % by weight | | | | | | | | | | | | | | |
| Polybutylene terephthalate 1 | % by weight | 100 | 75 | 75 | 75 | 75 | 75 | | | | | | | | |
| Polybutylene terephthalate 2 | % by weight | | | | | | | 52 | 52 | | | | | | |
| Nylon-6,6 | % by weight | | | | | | | | | 70 | 52 | 52 | 52 | | |
| Nylon-6 | % by weight | | | | | | | | | | | | | 52 | |
| Polystyrene | % by weight | | | | | | | | | | | | | | 70 |
| Glass fibers 1 | % by weight | | | | | | | 30 | 30 | 30 | 30 | 30 | 30 | | |
| Glass fibers 2 | % by weight | | | | | | | | | | | | | 30 | |
| Viscosity number | — | 1072 | 719 | 758 | 1023 | 1034 | 995 | 716 | 1005 | — | — | — | — | — | — |
| Melt flow index, 275° C. | 2 cm$^3$/min | — | — | — | — | — | — | — | — | 5.8 | 16.7 | 4.1 | 5.6 | 4.9 | — |
| UL 94 classification | | — | ncl | V-2 | V-2 | V-0 | V-0 | V-0 | V-1 | V-0 | ncl | V-2 | V-0 | V-0 | V-0 |

The invention claimed is:

1. A dialkylphosphinic salt or a mixture of dialkylphosphinic salts of the formula (I)

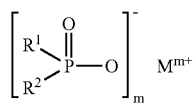

where
R$^1$, R$^2$ identical or different, are C$_1$-C$_6$-alkyl, linear or branched
M is Mg, Ca, Al, Sb, Sn, Ge, Ti, Fe, Zr, Zn, Ce, Bi, Sr, Mn, Li, Na, K or a protonated nitrogen base;
m is from 1 to 4;
having at least one telomer, wherein the telomer content is from 0.01 to 6% by weight and the at least one telomer is selected from the group consisting of ethylbutylphospinic salts, butylbutylphosphinic salts, ethylhexylphosphinic salts, butylhexylphosphinic salts, and hexylhexylphosphinic salts.

2. The dialkylphosphinic salt or mixture of dialkylphosphinic salts as claimed in claim 1, wherein the telomer content is from 0.1 to 5% by weight.

3. The dialkylphosphinic salt or mixture of dialkylphosphinic salts as claimed in claim 1, wherein the telomer content is 0.2 to 2.5% by weight.

4. The dialkylphosphinic salt or mixture of dialkylphosphinic salts as claimed in one claim 1, wherein M is aluminum, calcium, titanium, zinc, tin, or zirconium.

5. The dialkylphosphinic salt or mixture of dialkylphosphinic salts as claimed in one claim 1, wherein R$^1$ and R$^2$, are identical or different, and are methyl, ethyl, n-propyl, isopropyl, n-butyl, isobutyl, tert-butyl, n-pentyl, isopentyl, n-hexyl or isohexyl.

6. The dialkylphosphinic salt or mixture of dialkylphosphinic salts as claimed in claim 1, wherein the dialkylphosphinic salt or mixture of dialkylphosphinic salts is selected from the group consisting of aluminum tris(diethylphosphinate), zinc bis(diethylphosphinate), titanyl bis(diethylphosphinate), titanium tetrakis(diethylphosphinate) and mixtures thereof.

7. The dialkylphosphinic salt or mixture of dialkylphosphinic salts as claimed in claim 1, wherein the residual moisture level is from 0.01 to 10% by weight.

8. The dialkylphosphinic salt or mixture of dialkylphosphinic salts as claimed in claim 1, having a particle size from 0.1 to 1000 µm.

9. A flame retardant composition comprising a dialkylphosphinic salt or mixture of dialkylphosphinic salts as claimed in claim 1.

10. A flame retardant composition comprising from 50 to 99.9% by weight of a dialkylphosphinic salt or mixture of dialkylphosphinic salts as claimed in claim 1, and from 0.1 to 50% by weight of at least one additive.

11. The flame retardant composition as claimed in claim 10, comprising from 95 to 70% by weight of the dialkylphosphinic salt or mixture of dialkylphosphinic salts, and from 5 to 30% by weight of at least one additive.

12. The flame retardant composition as claimed in claim 10, wherein the at least one additive is selected from the group consisting of melamine phosphate, dimelamine phosphate, pentamelamine triphosphate, trimelamine diphosphate, tetrakismelamine triphosphate, hexakismelamine pentaphosphate, melamine diphosphate, melamine tetraphosphate, melamine pyrophosphate, melamine polyphosphate, melam polyphosphate, melem polyphosphate, and melon polyphosphate.

13. The flame retardant composition as claimed in claim 10, wherein the at least one additive is selected from the group consisting of oligomeric esters of tris(hydroxyethyl) isocyanurate with aromatic polycarboxylic acids, benzoguanamine, tris(hydroxyethyl) isocyanurate, allantoin, glycoluril, melamine, melamine cyanurate, urea cyanurate, dicyandiamide, and/or guanidine.

14. The flame retardant composition as claimed in claim 10, wherein the at least one additive is a zinc compound.

15. The flame retardant composition as claimed in claim 10, wherein the at least one additive is selected from the group consisting of carbodiimides (poly)isocyanates and styreneacrylic polymers.

16. The flame retardant composition as claimed in claim 10, wherein the average particle size of the flame retardant composition is from 0.1 to 3000 µm.

17. A flame-retardant polymer molding composition, comprising a polymer or a mixture of polymers and a dialkylphosphinic salt or mixture of dialkylphosphinic salts as claimed in claim 1.

18. The flame-retardant polymer molding composition as claimed in claim 17, further comprising
from 1 to 50% by weight of the dialkylphosphinic salt or mixture of dialkylphosphinic,
from 1 to 99% by weight of the polymer or a mixture of polymers,
from 0 to 60% by weight of at least one additive, and
from 0 to 60% by weight of at least one filler.

19. The flame-retardant polymer molding composition as claimed in claim 17 further comprising
from 5 to 30% by weight of the dialkylphosphinic salt or mixture of dialkylphosphinic salts,
from 5 to 90% by weight of the polymer or mixture of polymers,
from 5 to 40% by weight of, at least one additive, and
from 5 to 40% by weight of at least one filler.

20. The flame retardant polymer molding composition as claimed in claim 17, wherein the polymer or mixture of polymers is selected from the group of consisting of thermoplastic polymers and thermosetting polymers.

21. The flame-retardant polymer molding composition as claimed in claim 17, wherein the residual moisture level is from 0.01 to 10% by weight.

22. A process for preparation of a flame-retardant polymer molding composition comprising the steps of mixing a dialkylphosphinic salt or mixture of dialkylphosphinic salts as claimed in claim 1 with at least one polymer, wherein the at least one polymer is in pellet form, in a mixer to form a mixture, homogenizing the mixture in a compounding assembly at a temperature at or above the melting temperature of the at least one polymer to form a homogenized polymer extrudate, drawing off the homogenized polymer extrudate, cooling the homogenized polymer extrudate, and dividing the homogenized polymer extrudate into portions.

23. The process as claimed in claim 22, wherein the compounding assembly is selected from the group consisting of single-screw extruders, multisection screws, and twin-screw extruders.

24. The process as claimed in claim 22 wherein
the at least one polymer is polystyrene and the temperature is from 170 to 200° C., or
the at least one polymer is polypropylene and the temperature is from 200 to 300° C., or the at least one polymer is polyethylene terephthalate (PET) and the temperature is from 250 to 290° C., or the at least one polymer is polybutylene terephthalate (PBT) and the temperature is from 230 to 270° C., or the at least one polymer is nylon-6 (PA 6) and the temperature is from 260 to 290° C., or the at least one polymer is nylon-6.6 (PA 6.6) the temperature is from 260 to 290° C., or the at least one polymer is polycarbonate are the temperature is from 280 to 320° C.

25. The process as claimed in claim 22, wherein the compounding assembly is an extruder and wherein the effective screw length of the extruder as a multiple of the diameter of the screw is from 4 to 200 D.

26. A flame-retardant polymer comprising a dialkylphosphinic salt or mixture of dialkylphosphinic salts as claimed in claim 1, wherein the flame-retardant polymer is in the form of a molding, film, filament, or fiber.

27. The flame-retardant polymer as claimed in claim 26, further comprising
from 1 to 50% by weight of the dialkylphosphinic salt or mixture of dialkylphosphinic salts,
from 1 to 99% by weight of a polymer or a mixture of polymers,
from 0 to 60% by weight of at least one additive, and
from 0 to 60% by weight of at least one filler.

28. The flame-retardant polymer as claimed in claim 26, further comprising
from 5 to 30% by weight of the dialkylphosphinic salt or mixture of dialkylphosphinic salts,
from 5 to 90% by weight of a polymer or a mixture of polymers,
from 5 to 40% by weight of at least one additive, and
from 5 to 40% by weight of at least one filler.

29. A process for production of a flame-retardant polymer molding comprising the steps of processing a flame-retardant polymer molding composition as claimed in claim 17 at or above the melting temperature of the polymer or mixture of polymers, wherein the processing step occurs by injection molding compression molding, foam injection molding, internal gas pressure injection molding, blow molding, cast-film production, calendering, laminating, or coating.

30. The process as claimed in claim 29, wherein the polymer or mixture of polymers is a polymer and wherein
the polymer is polystyrene and the temperature is from 200 to 250° C., or
the polymer is polypropylene and the temperature is from 200 to 300° C., or
the polymer is polyethylene terephthalate (PET) and the temperature is from 250 to 290° C., or
the polymer is polybutylene terephthalate (PBT) and the temperature is from 230 to 270° C., or
the polymer is nylon-6 (PA 6) and the temperature is from 260 to 290° C., or
the polymer is nylon-6.6 (PA 6.6) and the temperature is from 260 to 290° C., or
the polymer is polycarbonate and the temperature is from 280 to 320° C.

31. The dialkylphosphinic salt or mixture of dialkylphosphinic salts as claimed in claim 1, wherein the residual moisture level is from 0.1 to 1% by weight.

32. The dialkylphosphinic salt or mixture of dialkylphosphinic salts as claimed in claim 1, having a particle size from 50 to 500 μm.

33. The dialkylphosphinic salt or mixture of dialkylphosphinic salts as claimed in claim 1, having a particle size from 10 to 100 μm.

34. The flame retardant composition as claimed in claim 14, wherein the zinc compound is selected from the group consisting zinc oxide, zinc hydroxide, zinc oxide hydrate, zinc carbonate, zinc stannate, zinc hydroxystannate, zinc silicate, zinc phosphate, zinc borate and zinc molybdate.

35. The flame retardant composition as claimed in claim 10, wherein the at least one additive is carbonylbiscaprolactam.

36. The flame retardant composition as claimed in claim 10, wherein the average particle size of the flame retardant composition is from 0.1 to 1000 μm.

37. The flame retardant composition as claimed in claim 10, wherein the average particle size of the flame retardant composition is from 1 to 100 μm.

38. The flame-retardant polymer molding composition as claimed in claim 17, wherein the residual moisture level is from 0.1 to 1% by weight.

39. The process as claimed in claim 22, wherein the mixing step further comprises mixing at least one additive with mixture.

40. The process as claimed in claim 22, wherein the compounding assembly is an extruder and wherein the effective screw length of the extruder as a multiple of the diameter of the screw is from 10 to 50 D.

41. A flame retardant polymer molding composition made in accordance with the process of claim 22.

42. A flame-retardant polymer molding made in accordance with the process of claim 29.

* * * * *